(12) United States Patent
Vanderveen et al.

(10) Patent No.: US 7,206,715 B2
(45) Date of Patent: Apr. 17, 2007

(54) EMPTY CONTAINER DETECTION USING CONTAINER SIDE PRESSURE SENSING

(75) Inventors: Timothy W. Vanderveen, Poway, CA (US); Robert D. Butterfield, Poway, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 449 days.

(21) Appl. No.: 10/750,082

(22) Filed: Dec. 31, 2003

(65) Prior Publication Data

US 2005/0145009 A1 Jul. 7, 2005

(51) Int. Cl.
*G06F 15/00* (2006.01)

(52) U.S. Cl. ...................... 702/138; 702/127
(58) Field of Classification Search .................. 604/81; 702/98, 100, 127, 138
See application file for complete search history.

(56) References Cited

U.S. PATENT DOCUMENTS

| | | | |
|---|---|---|---|
| 4,394,862 A | 7/1983 | Shim | |
| 4,430,074 A | 2/1984 | Mooring | |
| 4,530,696 A | 7/1985 | Bisera et al. | |
| 4,533,347 A | 8/1985 | Deckert | |
| 4,553,958 A | 11/1985 | LeCocq | |
| 4,617,014 A | 10/1986 | Cannon et al. | |
| 4,650,464 A | 3/1987 | Ruiz et al. | |
| 4,673,389 A | 6/1987 | Archibald et al. | |
| 4,681,563 A | 7/1987 | Deckert et al. | |
| 4,690,673 A | 9/1987 | Bloomquist | |
| 4,696,671 A | 9/1987 | Epstein et al. | |
| 4,705,506 A | 11/1987 | Archibald | |
| 4,710,166 A | 12/1987 | Thompson et al. | |
| 4,714,463 A | 12/1987 | Archibald et al. | |
| 4,769,001 A | 9/1988 | Prince | |
| 4,816,019 A | 3/1989 | Kamen | |
| 4,828,545 A | 5/1989 | Epstein et al. | |
| 4,836,752 A | 6/1989 | Burkett | |
| 4,838,856 A | 6/1989 | Mulreany et al. | |
| 4,850,972 A | 7/1989 | Schulman et al. | |
| 4,865,584 A | 9/1989 | Epstein et al. | |
| 4,882,575 A | 11/1989 | Kawahara | |
| 4,898,576 A | 2/1990 | Philip | |
| 4,938,072 A | 7/1990 | Brown et al. | |
| 4,946,439 A | 8/1990 | Eggers | |
| 4,979,940 A | 12/1990 | Bobo, Jr. et al. | |
| 4,998,914 A | 3/1991 | Wiest et al. | |
| 5,087,245 A | 2/1992 | Doan | |
| 5,088,981 A | 2/1992 | Howson et al. | |
| 5,096,385 A * | 3/1992 | Georgi et al. ................. | 417/18 |
| 5,100,380 A | 3/1992 | Epstein et al. | |

(Continued)

FOREIGN PATENT DOCUMENTS

WO WO 01/88828 A2 11/2001

*Primary Examiner*—Michael Nghiem
*Assistant Examiner*—Douglas N. Washburn
(74) *Attorney, Agent, or Firm*—Fulwider Patton LLP (57) ABSTRACT

A system and method for monitoring changes in the pressure of a fluid line upstream of an infusion pump to determine when a fluid container has emptied, and to provide a signal indicating that the container needs replacement or replenishment. The difference between averaged pressures over separate time periods is monitored to determine when the fluid container is empty. The system and method are applicable to primary and secondary fluid container setups and can detect the point where the secondary has been emptied and the primary flow has resumed.

16 Claims, 4 Drawing Sheets

U.S. PATENT DOCUMENTS

| | | |
|---|---|---|
| 5,108,367 A | 4/1992 | Epstein et al. |
| 5,154,700 A | 10/1992 | Dansby |
| 5,304,126 A | 4/1994 | Epstein et al. |
| 5,312,334 A | 5/1994 | Hara et al. |
| 5,356,378 A | 10/1994 | Doan |
| 5,423,743 A | 6/1995 | Butterfield |
| 5,423,749 A | 6/1995 | Merte et al. |
| 5,464,392 A | 11/1995 | Epstein et al. |
| 5,554,115 A | 9/1996 | Thomas et al. |
| 5,803,917 A | 9/1998 | Butterfield et al. |
| 5,935,106 A | 8/1999 | Olsen |
| RE36,871 E | 9/2000 | Epstein et al. |
| 6,213,972 B1 | 4/2001 | Butterfield et al. |
| 6,847,899 B2 * | 1/2005 | Allgeyer ............ 702/32 |
| 2001/0023345 A1 | 9/2001 | Wolff et al. |

* cited by examiner

EMPTY CONTAINER DETECTION USING CONTAINER SIDE PRESSURE SENSING

BACKGROUND OF THE INVENTION

1. Field of the Invention

The present invention generally relates to a system and method for determining when an infusion fluid container has emptied, or is about to empty, as a result of fluid being withdrawn from the container. More specifically, the present invention relates to a system including an infusion pump having a sensor that is capable of monitoring and detecting pressure within the container-side of a fluid "infusion set" so as to determine when the associated fluid container is empty, or about to become empty. Upon such detection, the system may provide a local or remote audible and/or visual alert to a caregiver administering or monitoring the infusion and may initiate pre-programmed changes to the flow of fluid including changing to an alternate flow rate or stopping infusion.

2. General Background and State of the Art

Infusion of therapeutic fluids to treat or nourish patients is commonly used in hospitals and other medical care institutions. Originally such infusions were carried out by hanging a bag or container of therapeutic fluid from a pole so that fluid flows under the force of gravity regulated by a user-controllable restrictor through a length of tubing and into the lumen of a vessel of a patient. More recently, the flow of fluid into the patient is under the control of a programmed infusion pump located in the fluid pathway. Infusion pumps are useful in that they allow for more precise control of the flow of therapeutic fluid into the patient. For example, using an infusion pump, relatively precise amounts of fluid may be infused at controlled rates. Moreover, the rate of infusion may be altered during the infusion by programming the pump to pump the fluid at a different rate. This capability is useful where a bolus of therapeutic fluid is desired to initiate an infusion regimen, with the rate then being decreased to a reduced flow rate for the remainder of the infusion. When a pump is located in the fluid pathway, the portion of the tubing between the container of medical fluid and the pump is referred to as the "container-side" fluid line.

One problem that exists with all infusions is that it is difficult to monitor and determine when the fluid container becomes empty, necessitating a change of container or other attention from a care-giver. In the case of a simple primary infusion, when the fluid container is emptied, the flow rate is typically reduced from the flow rate prescribed by a physician to a "keep vein open" or KVO rate. If the empty or nearly empty container is not replaced or replenished, air may enter the infusion line, which is generally considered to be an undesirable condition. In the case of "secondary" infusion, a fluid container containing a different IV solution is attached to the container-side primary fluid line and its fluid is infused temporarily in lieu of the primary fluid until the secondary container is empty. In these infusions attention must be given to the secondary fluid container so that air does not enter into the infusion line.

One method used to monitor the state of the fluid container has been to estimate the volume of fluid in the secondary container and program the secondary mode of the pump to deliver this volume. This method is prone to errors due to mistakes or inaccurate estimations of the fluid infusion rate or the amount of fluid remaining in the container.

In many secondary infusion systems, a one-way check valve is inserted in the primary fluid path and the primary container is lowered below the secondary container, typically, for example, about eight inches. The secondary fluid enters the main intake fluid pathway through a port in the main fluid line. When the secondary container is filled, the pressure exerted against the check valve prevents flow of the primary fluid into the fluid line. When the secondary fluid container is emptied to a level slightly below that of the top of the fluid in the primary container, the pressure against the check valve reduces to the point that it opens, permitting the primary fluid to once again flow into the infusion line.

In many cases where secondary infusion of a fluid is performed, the desired rate of secondary fluid flow is different from the desired rate of primary fluid flow. Accordingly, an operator must preset the infusion pump with the estimated volume in the secondary container, so that when the pump has infused that amount at the prescribed secondary rate, the pump will automatically transition to the primary flow rate. However, frequent errors due to incorrect estimation of container volume or inaccurate setting of the secondary volume-to-be-infused renders this method unreliable, requiring frequent monitoring by care-givers to ensure that the proper fluid is being infused at the proper rate, and to prevent air from entering into the infusion line in the instance of a fault such as a non-flowing checkvalve.

In some infusion tubing setups, there may be multiple infusion lines connected together via a manifold or similar device providing fluid to a common vascular access device. Such a system allows two or more therapeutic fluids to be infused into the patient in a programmed sequence. For example, the care-giver may prescribe a therapeutic regimen requiring the infusion of a primary fluid for a first set length of time, a secondary fluid for a second set length of time, and then a third fluid for a third set length of time, followed by infusion of the secondary fluid. In many cases, the various therapeutic fluids are not compatible with each other, and so care must be taken to avoid mixing the fluids in the manifold. While current pumps can be programmed to deliver the exemplary therapeutic regimen described above, as with the other examples, errors in setting the pumps for the volumes to be infused, or the occurrence of an empty container, can complicate the delivery of the infusion fluids and require frequent monitoring during the infusion.

Another attempt to determine when a container is empty involved trying to sense the vibration produced by drops falling into a drip chamber. Cessation of these vibrations meant that drops were no longer falling, indicating that the container was empty. However, noise sources such as patient or equipment movement, cross coupling between fluid lines or pumping channels made this approach difficult to carry out in practice.

What has been needed, and heretofore unavailable, is an inexpensive yet reliable system and method for detecting when an infusion container is empty, or nearly empty, and for providing a signal to an infusion pump to either alter the infusion rate, provide an alert signal to a care-giver that the container needs replenishment or replacement, or switch to a different infusion source. What is further needed is a reliable system and method for use with automatic secondary infusion setups that provide detection of the occurrence of transition from flow of the secondary fluid to flow of the primary fluid. The present invention satisfies these and other needs.

INVENTION SUMMARY

Briefly and in general terms, the system and method in accordance with the invention are directed to monitoring the pressure of a fluid line connecting a fluid container with an infusion pump. A pressure sensor monitors the pressure within the fluid line as fluid is drawn from the fluid container by the infusion pump. A processor in communication with the pressure sensor samples at a selected frequency pressure signals generated by the pressure sensor representative of the pressure within the fluid line. At the conclusion of a selected period of time, the processor averages the values of the sampled pressure signals received during the period of time, and stores the averaged value in a memory that is accessible by the processor. After a second period of time has elapsed, a second averaged value is calculated using the sampled signals received during the second period of time. The processor then compares the averaged value from the second period of time to the averaged value from the first period of time to determine if there is a difference that reaches a predetermined threshold. If the predetermined threshold is exceeded, the processor provides a signal indicating that the predetermined threshold has been exceeded.

In another aspect, the present invention is embodied in a system for determining when a fluid container connected to an infusion pump by an infusion line has been emptied of fluid and comprises: a pressure sensor in operable communication with the fluid line, the pressure sensor capable of monitoring a pressure within the fluid line and providing a signal representative of the monitored pressure; a memory for storing pressure-related values; and a processor in operable communication with the pressure sensor and the memory, the processor programmed to receive signals from the pressure sensor and sample the received signals at selected intervals, the processor also programmed to calculate a first averaged sampled pressure value from the signals received during a first selected interval and store the first averaged sampled pressure value in the memory, the processor also programmed to compare the stored averaged sampled pressure value with a second averaged sampled pressure value calculated during a second selected interval and provide a signal if the comparison results in a difference between the first and second calculated averaged sampled pressure values reaches a predetermined threshold. In a more detailed aspect, the pressure sensor is located within a housing of the infusion pump. In further detail, the processor is also located within the housing of the infusion pump and in yet even further detail, the processor is located at a position remote from the infusion pump.

In still another aspect in accordance with the invention, a system is provided wherein the processor is in communication with an information system of an institution, and wherein the signal is communicated to the information system for dissemination to at least one care giver within the institution. In another embodiment, the processor is part of a local network.

In a further more detailed aspect, the sampling period is determined by counting the number of pump mechanism cycles that have occurred, and then calculating the averaged value when a selected number of cycles have been completed.

In yet another aspect in accordance with the invention, a method is provided for detecting when a fluid container has emptied during the course of an infusion. The method comprises the steps of sampling the pressure within an infusion line connecting a fluid container with an infusion pump at a selected frequency, calculating a first averaged sampled pressure value by averaging the sampled pressure over a selected period of time, storing the averaged sampled pressure value in a memory, calculating a second averaged sampled pressure value by averaging the sampled pressure over a second selected period of time, calculating a difference between the first averaged sampled pressure value and the second averaged sampled pressure value, and providing a signal if the difference reaches a pre-determined threshold value. In another aspect, the method further comprises the steps of continuously sampling the pressure within the infusion line and calculating averaged sampled pressure values, incrementing the selected period of time for each calculation, comparing the latest averaged sample pressure value to a selected previous averaged sampled pressure value and calculating a difference between the latest averaged sample pressure value and the selected previous averaged sampled pressure value, and providing a signal if the difference reaches a pre-determined threshold value.

In a further aspect, the step of providing a first signal comprises providing an indication that the container is empty. In another aspect, the step of providing the second signal comprises providing an indication that a drip chamber associated with the container is empty.

Other features and advantages of the invention will become apparent from the following detailed description, taken in conjunction with the accompanying drawings, which illustrate, by way of example, the features of the invention

DETAILED DESCRIPTION OF THE PREFERRED EMBODIMENTS

Figure 1:
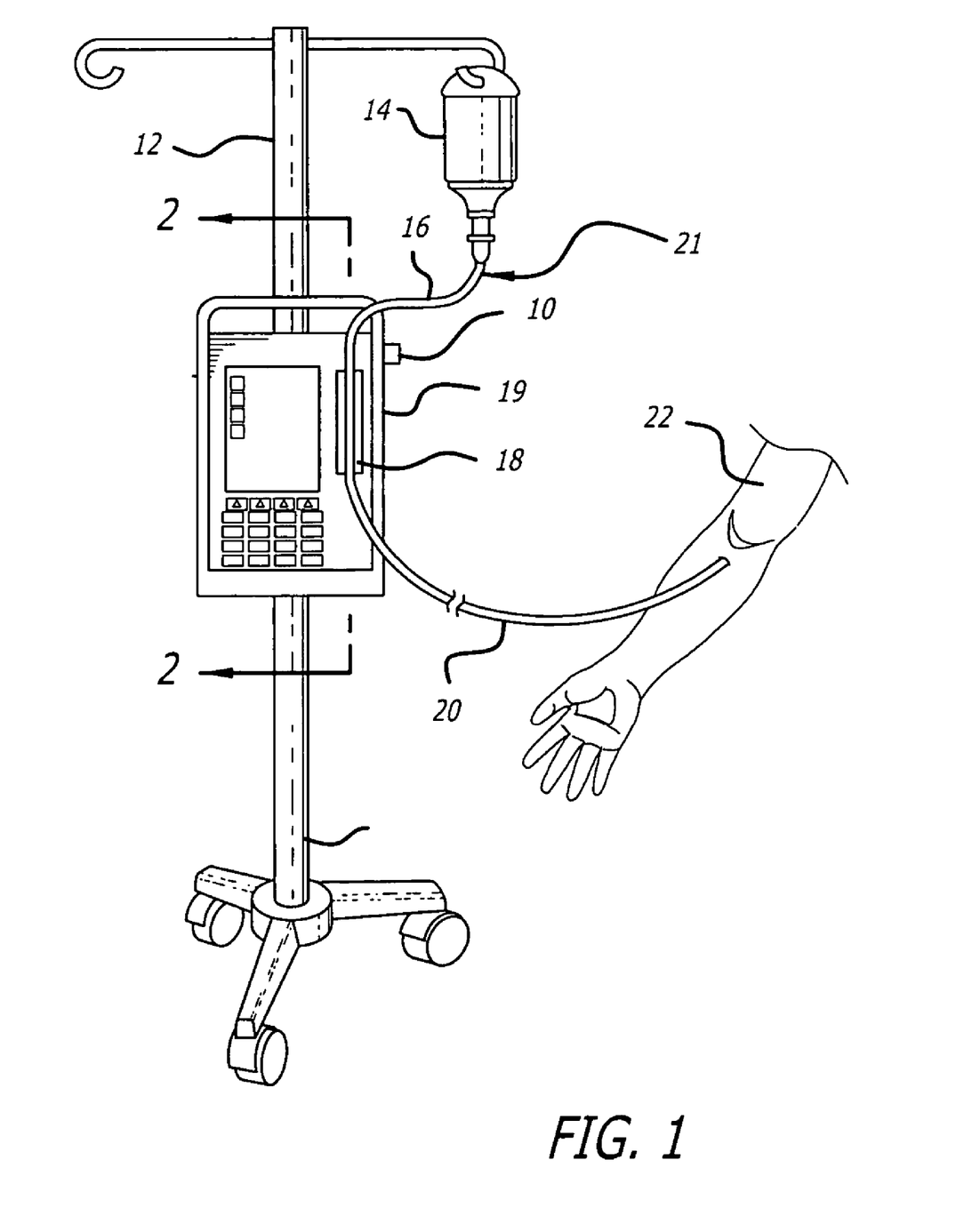
FIG. 1 depicts an infusion set-up including a fluid source and an infusion pump for infusing fluid from the fluid source into a patient.

Referring now to FIG. 1, there is shown an infusion pump set-up, generally designated 10, shown in use in its intended environment. In particular, the infusion pump set-up 10 is shown mounted to an intravenous (I.V.) pole 12 on which a fluid source 14 containing an I.V. fluid is held. The fluid source 14 is connected in fluid communication with an upstream fluid line 16. The upstream fluid line 16 is a conventional I.V. infusion-type tube typically used in a hospital or medical environment, and is made of any type of flexible tubing appropriate for use to infuse therapeutic fluids into a patient, such as polyvinylchloride (PVC). The upstream fluid line 16 is connected with another tube portion 18 that is flexible and is mounted in operative engagement with a peristaltic pumping apparatus 19, for propelling fluid through a downstream fluid line 20, for example, to a patient's arm 22. It will be understood by those skilled in the art that the upstream fluid line 16, the flexible portion fluid line 18, and the downstream fluid line 20 may be portions of a continuous length of flexible tubing, with the portions defined by the location of the peristaltic pump 19. For convenience in reference, the overall length of tube has been given the reference numeral of 21 in FIGS. 1 and 2. In this context, the term "upstream" refers to that portion of the flexible tubing that extends between the fluid source and peristaltic pump, and the term "downstream" refers to that portion of the flexible tubing that extends from the peristaltic pump to the patient. For convenience, the overall tube extending between the.

Figures 2, 5:
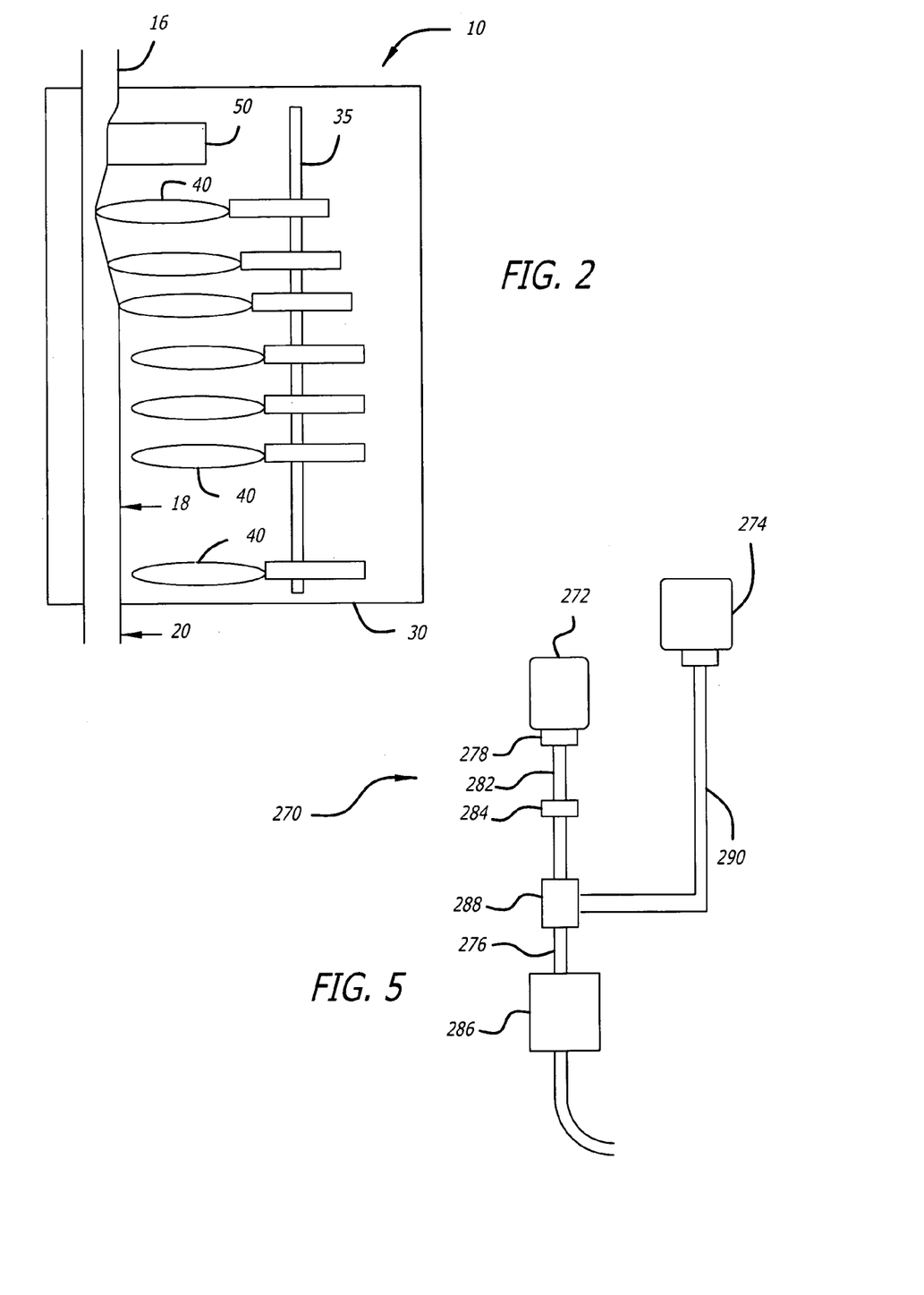
FIG. 2 is a schematic side view of an exemplary peristaltic infusion pump including an upstream pressure sensor.
FIG. 5 shows an infusion set up with primary and secondary fluid containers both connected to the same fluid line to infuse fluid to the patient, showing that the secondary container is higher than the primary container.

FIG. 2 depicts an enlarged schematic view of the pumping mechanism of the infusion pump 10 showing the interaction of the infusion tube with the elements of the peristaltic infusion pump. The fluid line 16 is disposed in the housing 30 of the pump 10 in such a manner that the flexible portion 18 of the infusion line is in releasable contact with one or more fingers 40 of the peristaltic infusion pump. Typically, such a peristaltic infusion pump utilizes a camshaft 35, or other mechanism, to actuate one or more fingers 40 so that one or more fingers 40 sequentially press upon and squeeze the flexible portion 18 of the tube to displace fluid within the tube in a downstream direction. The downstream segment 20 of the tube of the fluid administration set 21 is also partially shown. Various details of a complete peristaltic mechanism have been left out of FIG. 2 so that clarity of illustration of the above-discussed features is retained. However, one skilled in the art will understand that many other mechanical components can exist with such a mechanism.

An upstream pressure sensor or detector 50 is mounted in the housing of the pump 10 to monitor the fluid pressure within the upstream tube 16. The upstream pressure sensor 50 may be any kind of detector known in the art that is capable of monitoring the fluid pressure within the tube 16 and providing signals that may be received by suitable electronics, such as, for example an A/D converter and a storage medium, such as a flash memory, or other type of suitable storage medium for storing digital values representative of the signals provided by the sensor. The signals may also be provided to a computer or microprocessor for analysis, display or reporting. Examples of pressure sensors or detectors suitable for monitoring the pressure within an upstream infusion line are silicon strain gauges, resistive strain beams or other sensors or detectors known to those skilled in the art.

Those skilled in the art will also understand that the upstream pressure sensor 50 and methods described herein are equally applicable to any displacement type infusion pump, and such is intended to be within the scope of the present invention. Even further, the principles may be employed even in pumps or servo-controlled gravity flow regulators. Moreover, while the present invention is described in relation to an infusion pump having a processor or computer associated with the pump, it is intended that the invention also include systems wherein the microprocessor or computer is remote from, but in communication with the pump.

Figure 3:
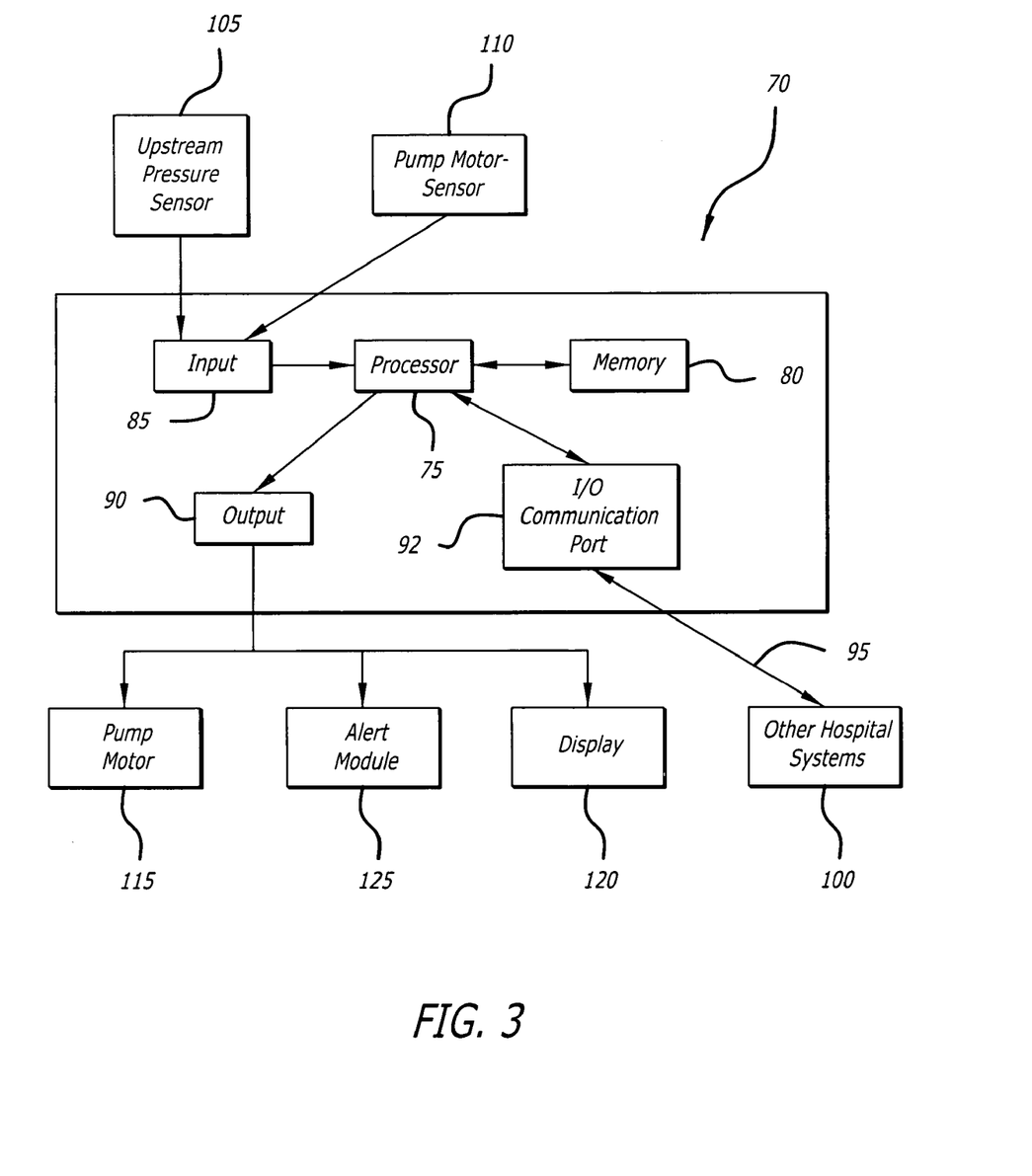
FIG. 3 is a schematic block diagram of one embodiment of an infusion pump controller capable of being programmed to carry out the present invention.

Generally, as shown in FIG. 3, the infusion pump 10 will include a controller 70 configured or programmed to control the operation of the peristaltic infusion pump so that a prescribed amount of medication or other therapeutic fluid is infused into the patient over a desired period of time. Such controllers typically include a microprocessor 75, a memory 80 associated with the microprocessor 75, one or more inputs 85 for inputting signals to the microprocessor, and one or more outputs 90 for outputting signals from the microprocessor.

The controller 70 may also be in communication with other systems, such as a pharmacy information system, hospital administration system, or other such systems in the institution using an input/output communications port 92 and a communication means 95. The input/output communications port 92 may be any port configured to send and receive data using appropriate communication protocols, such as RS232 and the like. For example, the input/output communications port 92 may be a serial port, a parallel port, a USB, or other suitable port. It will also be understood that the input 85 and the output 90 may be combined in such a manner that all signals to and/or from the processor are communicated through one or more input/output ports 92, rather than through separate inputs and outputs.

The communication means 95 may be a hard wired or wireless connection to another computer, a local area network, a wide area network, a telephone line to a remote server or client system, or the Internet. The communication means may include specialized connection devices for connecting to optical fiber, coaxial cable, Ethernet cabling, or other communication lines. Alternatively, wireless connections may be used, which may also include the use of suitable transmitters and receivers as is known in the art. Such wireless connectivity may include use of infra red, RF, Bluetooth or WiFi (IEEE 802.11b) communication means and the like. Additionally, the microprocessor 75 is commonly programmed using either embedded programming instructions or suitable software so that the microprocessor can carry out the tasks desired of it.

In one embodiment of the system and method of the present invention, the microprocessor 75 is capable of receiving signals from an upstream pressure sensor 105 through the input 85 (typically an amplifier and A/D converter). The upstream pressure sensor 105 is disposed adjacent an upstream infusion line so as to monitor the pressure within the upstream infusion line, and provide signals representative of the sensed pressure within the infusion line to the microprocessor 75. The microprocessor 75, as described above, is programmed using appropriate software or embedded commands to analyze the signals received from the upstream pressure sensor 75. After analysis of the received upstream pressure signals is completed, the processor may output a signal through the output 90. This signal output may be directed to the pump motor 115 to control the infusion of fluid to the patient.

The output signal may also be directed to a display 120 to inform an operator of the status of the pump and/or the pressure within the upstream infusion line. This display may also include a means of providing a visual alert, such as a flashing display, blinking light, or a change in text color on the display to alert an operator that the infusion set-up requires attention.

The output signal may also be directed to an alert module 125. This alert module may be a separate module of the processor 75 that is controlling the pump 10, or it may be located at a location remote from the pump, and/or associated and in communication with a separate processor remote from the pump. The alert module 125 may be configured to provide visual, auditory, or a combination of visual and auditory notifications to care givers to alert the care giver that attention must be given to the infusion system. The alert module may produce signals that are communicated to consoles at the bed side, the nurse station, or a centrally located monitoring system. Additionally, various combinations of display changes and auditory alerts may be used to signify a priority of an alert, so that alerts which do not require immediate attention are less noticeable than alerts that require immediate attention to correct a problem before harm to the patient being infused can occur.

The alert module 125 may also provide signals representing the progress of the infusion, including any alerts generated due to a sensed reduced or negative pressure in the upstream infusion line 16 (FIG. 1), to a database where the information is stored for later inspection and analysis. The database may be associated with the pump 10, or the database may be remote from the pump. For example, where the pump is controlled by a remote controller, the database may be located and associated with the remote controller. In another embodiment, the database may be part of an institutional information system which may be part of an enterprise wide network.

In another embodiment, the microprocessor 75 may also be configured to receive signals from a pump motor sensor 110 through the input 85. In this embodiment, the processor 75 may monitor the function of the pump, collecting, analyzing, and storing information related to the infusion, such as, for example, the start time and completion time of the infusion, the amount of fluid infused, and the number of pump cycles that have been completed since the start of the infusion or since a selected time in the past. This information may be stored in the memory 80 for later retrieval and analysis, or the information may be communicated to another, remote, system using the communication means 95.

Figure 4:
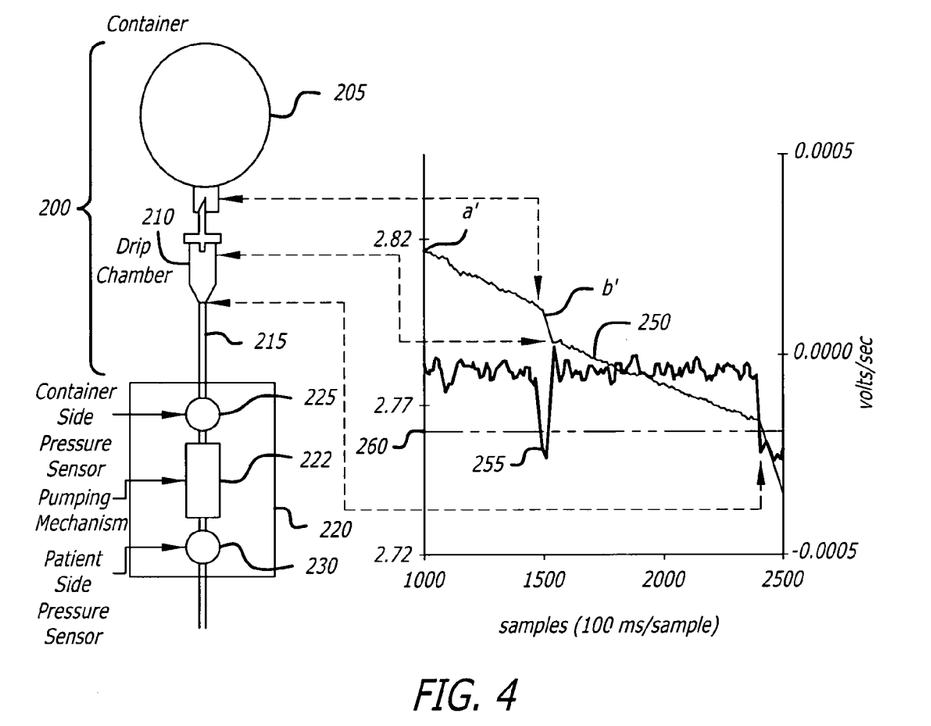
FIG. 4 depicts an infusion set up showing a container, drip chamber, infusion line and infusion pump with a container side (upstream) pressure sensor, and a graph of sampled pressure measurements over time as fluid is withdrawn from the chamber, the graph illustrating the detection of an empty container in accordance with one embodiment of the present invention.

FIG. 4 illustrates the design and software analysis of an embodiment of the present invention. In this embodiment, the upstream portion 200 of an infusion setup is shown. Such an infusion set up typically comprises a fluid container 205 that is filled with an I.V. fluid. To facilitate priming of the infusion set, avoid entrainment of air bubbles and provide visualization of the infusion, a drip chamber 210 is generally located adjacent the bottom of the container 205. A length of flexible infusion line extends from the bottom of the drip chamber and into the infusion pump 220. The infusion pump 220 includes an upstream, or container side pressure sensor 225, and typically also includes a patient side pressure sensor 230 as well as a pumping mechanism 222, such as a peristaltic mechanism.

As fluid is withdrawn from the container 205, the level of fluid falls. The upstream pressure sensor 225 in one embodiment senses the resulting decrease in pressure within the infusion line 215. The pressure within the infusion line 215 is dependent on the amount of fluid in the container 205 and the rate of flow of fluid through the fluid line.

The change in pressure within the infusion line 215 as an infusion progresses is illustrated by the graph in FIG. 4. During an infusion, the processor controlling the infusion pump motor also samples the output of the upstream pressure sensor 225. Typically, the upstream pressure sensor is sampled about once every 100 milliseconds, although other sampling rates may be used. Because the mechanism 222 does not draw fluid absolutely smoothly, small variations of intake flow rate throughout a mechanical cycle through the fluidic impedance to flow of the upstream tubing 215 produce small pressure changes in the upstream infusion line 215. The amount of fluid pumped during a cycle is dependent on the particular pump being used. For example, the MEDLEY® Large Volume Pump Module (LVP) manufactured and sold by ALARIS Medical Systems, Inc., San Diego, Calif., typically draws and expels 165 microliters of fluid volume during each cycle.

In one embodiment of the present invention, the upstream sensor 225 is sampled synchronously with the movement of the pump mechanism 222 to account for artifacts in the pressure signal caused by the variation in flow during a cycle. Since the fluctuations are cyclic with each revolution of the mechanism of the infusion pump 220, the cycle averaged pressure ("Pca"), which is an average of the sampled pressures detected by the pressure sensor during a single cycle. Pca is highly stable from cycle to cycle owing to the large number of samples typically measured. One added advantage of averaging the signal is that the averaging may start and stop at any point within the cycle and the averaged signal will produce equivalent results to calculations begun and ended at a different point. Further, pausing the pump, or changing the pumping rate will not affect the resultant Pca value. In a typical embodiment, the pressure sensed by the upstream pressure sensor 225 is sampled approximately 100 times per cycle. Thus, in the MEDLEY® LVP pump identified above, a pressure sample is obtained for about each 1.5–2.0 microliters of fluid drawn from the container.

The pressure sampling and analysis process is controlled by the processor associated with the infusion pump. As each sampled pressure is received by the processor, the processor may store the sampled pressure values in a buffer, cache, working memory, or other storage medium for later analysis. Periodically, typically at least once a cycle, the sampled pressure values are averaged to calculate the Pca. The values for the Pca signal may also be stored by the processor for further analysis, as will be disclosed in more detail below. Each stored Pca signal may also be associated with a value representing the number of cycles that had elapsed since the start of the infusion, or since the last Pca was determined. For example, the first Pca calculated could be associated with the number 1, the second Pca with the number 2, and so on, so that the series of Pca may be sequentially arranged in accordance with the number of cycles that are completed, providing a time frame for further analysis to determine the occurrence of sequential events.

As an infusion fluid container empties, the "head" pressure due to depth of the fluid within the upstream infusion line falls slowly, as can be seen from the line indicated by numeral 250 of the graph of FIG. 4, which is a line connecting pressure measurements indicated by volts at each sample. The sampled signal from the pressure sensor 225 may be further processed by calculating the difference between two Pca signals separated by one cycle. The "delta" value thus calculated is the slope of the Pca filtered pressure signal of line 250, and is illustrated by the line indicated by numeral 255 of the graph of FIG. 4, which shows the slope or rate of change or differential in units of volts per second. Differentiating the Pca signals in this manner is advantageous in that it enhances the sensitivity of the analysis, since for small containers, the pressure changes much more rapidly than the pressure where large fluid containers are used, and such large changes in pressure may result in false identification of an empty container, as will be discussed in more detail below.

Referring again to the graph of FIG. 4, the function of one embodiment of the present invention will be described. As fluid is removed from the container 205, the pressure within the fluid line 215 falls slowly and relatively constantly, as indicated by the line 250 of the graph. It is also apparent that the slope of the pressure drop is relatively constant, although magnification of the slope value by the choice of units on the axis of the graph causes the graph of the slope to appear somewhat jagged. The processor associated with the pump monitors the value of the slope, or delta signal, of line 250 that have been calculated as described above, and is typically programmed to ignore all changes in the slope of the signal that fall below a pre-determined threshold.

Because the amount of fluid being withdrawn from the container 205 by the pump 220 is relatively small compared to the volume of fluid within the container 205, the level within the container 205 falls relatively slowly. However, when the fluid surface level reaches the orifice of the drip chamber 210, which typically has less volume than the container 205, the amount of fluid removed during each sensor sampling results in a relatively large change in fluid level with each sample. This rapid reduction in the level of the fluid appears as a large negative delta signal at point b' of line 255. Similarly, once the drip chamber 210 empties, the fluid surface level enters the relatively small bore of the infusion line 215, resulting in a further pressure decrease and large negative delta, depicted at point c' on line 255.

As stated above, the processor 75 monitoring the pressure signal may be programmed to respond when a negative delta signal reaches a pre-determined threshold value, as illustrated by the line 260 of the graph of FIG. 4. When the delta signal reaches the threshold value represented by line 260, the logic of the processor is programmed to determine that the container has emptied. The processor may respond to such a threshold-exceeding event in a number of ways known to those skilled in the art, such as providing a visual or audible signal to a care-giver indicating that the infusion system needs attention. Alternatively, the processor may log the event in a memory that may be either associated with the processor, or located at location remote from the pump or processor, if the processor is in communication with an appropriate storage media by way of a network connection or some other means.

In another embodiment, the processor 75 may respond to a sufficiently large delta signal indicating an empty container 205 by operating one or more suitable valves to change containers, or to change between infusion lines or infusion sources or take another suitable action depending on the type of infusion regimen that has been programmed into the processor associated with the pump 220. This is particularly useful where more than one infusion line or source is connected to the pump by way of a manifold or other similar arrangement. For example, where the system detects that a secondary infusion container has been emptied, the processor may provide a command to the pump to change the rate of infusion to a keep-vein-open mode, or it may control the pump to begin pumping at a different rate suitable for infusion of fluid from the primary container.

In another embodiment, the processor 75 may store the occurrence of threshold exceeding delta signals so as to discriminate between the emptying of the container 205 and the emptying of the drip chamber 210. In this embodiment, a memory 80 associated with the processor may be indexed with a value indicating the start of the infusion. When the first delta signal that reaches a pre-determined threshold is detected, that value, or some representation of that value, or a flag indicating that a pre-determined threshold exceeding event has occurred, may be stored in the memory. When a second threshold-exceeding delta signal is detected, the logic of the processor, by comparing the sequencing of the threshold exceeding events, can determine which event occurred first in time, indicating that the container 205 is empty, and which event occurred later in time, indicating that the drip chamber 210 is empty. Such a determination is useful in ensuring that all, or nearly all of the fluid contained in the container 205 is infused into the patient, leaving only the relatively small volume remaining in the upstream infusion line 215, before sending an alert to a care-giver or monitor system that the container is empty and needs replenishment or replacement. Further, such determinations may be made by the processor depending on the infusion regimen prescribed. For example, in the case of a secondary infusion, the processor is able to determine when the secondary container is empty, and infusion switches to a primary container, and when the primary container is empty, so that it may provide an alert to the care giver or institution that replenishment or replacement of the fluid containers is required.

Turning now to FIG. 5, there is shown an infusion set up 270 with primary 272 and secondary 274 fluid containers both connected to the same container-side fluid line 276 to infuse fluid to the patient. Both the primary and the secondary fluid containers include a drip chamber 278 and 280 respectively. The primary line 282 includes a check valve 284 so that the secondary fluid will flow to the infusion pump 286. A fitting 288 connects the line 290 from the secondary to the container-side fluid line 276. FIG. 5 shows that the secondary container 274 is higher than the primary container 272 so that the fluid from the secondary will activate the check valve 284 to prevent fluid from the primary from flowing into the container-side fluid line 276. Although not shown, the infusion device 286 includes an upstream pressure sensor as is shown in FIG. 4.

Figure 6:
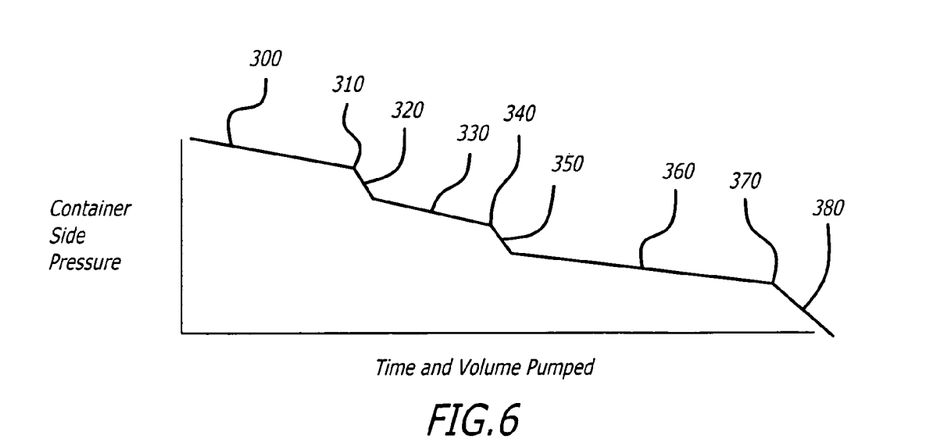
FIG. 6 presents a graph of the pressure waveform of the system of FIG. 5.

Referring now to both FIGS. 5 and 6, the flow of fluid through the infusion set up will be shown and the pressure waveform of the container-side fluid line is shown. The line segment 300 represents the pressure of the secondary container 274 which is falling slowly while there is fluid surface in the secondary container. When the fluid surface reaches the drip chamber cannula, as shown at point 310, the pressure will fall more rapidly, as indicated by the line 320. Once the fluid surface is in the drip chamber 280, the fluid pressure falls more slowly again 330. But when the fluid surface reaches the secondary line 290 as shown at point 340, the pressure falls rapidly, as indicated by the line 350. Once the fluid surface of the secondary line becomes level with the fluid surface in the primary container 272, the pressure change becomes small again as shown by line 360 because now the primary container is emptying. Finally when the primary container is emptied and the primary fluid enters its drip chamber 278 cannula, a rapid negative pressure drop occurs as shown by line 380.

The waveform of FIG. 6 can be considered to be a sort of "signature" of what is to be expected in a primary/secondary system such as that shown in FIG. 5. If the operator sets a secondary volume to be infused ("VTBI"), then by detecting the failure of this pattern or signature to occur within a pre-determined volume relative to the programmed secondary VTBI, a fault of the setup (such as a failure to open a clamp on the secondary line 290) could be determined and the operator alerted. Also, if the infusion continues for some selected time period beyond the programmed secondary VTBI without the appearance of the "return to primary" signature shown in FIG. 6, then a fault is determined.

Another use of the waveform, pattern, or signature shown in FIG. 6 is to automatically switch infusion rates. If the operator does not set a secondary VTBI, then by detecting the occurrence of the pattern of FIG. 6, the system will automatically determine that flow from the primary container has resumed. The pump could be automatically programmed to change its flow rate to the primary flow rate at that time.

While several particular embodiments of the invention have been illustrated and described, it will be apparent that various modifications can be made without departing from the spirit and scope of the invention.

We claim:

1. A method for detecting when a fluid container has emptied during the course of an infusion, comprising:

sampling pressure at a selected frequency within an infusion line connecting the fluid container with an infusion flow control device at a location of the infusion line between the container and a fluid movement mechanism forming a part of the infusion control device;

calculating a first averaged sampled pressure value by averaging sampled pressures sampled during a first selected period of time;

storing the first averaged sampled pressure value in a memory;

calculating a second averaged sampled pressure value by averaging sampled pressures sampled during a second selected period of time;

calculating a difference between the first averaged sampled pressure value and the second averaged sampled pressure value; and providing a signal if the difference reaches a pre-determined threshold value indicative of the level of fluid remaining in the container.

2. The method of claim 1 further comprising:

continuing to sample the pressure within the infusion line and calculating averaged sampled pressure values, incrementing the selected period of time for each calculation;

comparing a latest averaged sample pressure value to a next previous averaged sampled pressure value;

calculating a difference between the latest averaged sample pressure value and the next previous averaged sampled pressure value; and providing the signal indicative of the level of fluid remaining in the container if the difference reaches the pre-determined threshold value.

3. The method of claim 2 further comprising:

processing multiple averaged sample pressure values to provide a measure of a rate of change of the multiple averaged sample pressure values, and determining when the measure of the rate of change indicates the existence of a pre-defined condition within the infusion line.

4. The method of claim 1 wherein providing the signal indicative of the level of fluid remaining in the container provides an indication that the container is empty.

5. The method of claim 2 wherein providing the signal indicative of the level of fluid remaining in the container provides an indication that more than one container is empty.

6. The method of claim 1 further comprising the step of synchronizing the sampling with movement of the fluid movement mechanism that causes the fluid to flow from the fluid container.

7. The method of claim 1 further comprising the steps of sampling the pressure within an infusion line connecting a primary and a secondary fluid container with the fluid movement mechanism and based on the steps of calculating averaged sampled pressure values, storing averaged sampled pressure values, and calculating a difference, providing a first signal if the difference reaches a first threshold indicating that the secondary is empty, and providing a second signal if the difference reaches a second threshold indicating that the primary is empty.

8. A system for determining when a fluid container connected to an infusion pump having a pumping mechanism by an infusion line has been emptied of fluid, the system comprising:

a pressure sensor in operable communication with the fluid line and disposed at a location between the container and the pumping mechanism, the pressure sensor capable of monitoring a pressure within the fluid line and providing signals representative of pressure related values of the monitored pressure;

a memory adapted to store the pressure related values; and a processor in operable communication with the pressure sensor and the memory, the processor programmed to receive signals from the pressure sensor and sample the received signals at selected intervals, the processor also programmed to calculate a first averaged sampled pressure value from signals received during a first selected interval and store the first averaged sampled pressure value in the memory, the processor also programmed to compare the stored first averaged sampled pressure value with a second averaged sampled pressure value calculated from signals received during a second selected interval and provide a container empty signal if the comparison results in a difference between the first and second calculated averaged sampled pressure values reaches a predetermined threshold.

9. The system of claim 8 wherein the pressure sensor is located within a housing of the infusion pump.

10. The system of claim 8 wherein the processor is remote from the infusion pump.

11. The system of claim 8 wherein the processor is in communication with an information system of an institution, and wherein the container empty signal is communicated to the information system for dissemination to at least one care giver within the institution.

12. The system of claim 8 wherein the processor is programmed to count a number of revolutions of the pumping mechanism, and to calculate the averaged pressure value when a predetermined number of revolutions have been completed.

13. The system of claim 8 wherein the pressure sensor is disposed in direct contact with the fluid line.

14. The system of claim 8 wherein the processor is configured to sample the received signals in synchronization with movement of the pumping mechanism.

15. The system of claim 8 wherein the processor is further configured to sample the pressure within an infusion line that connects a primary and a secondary fluid container with the pumping mechanism.

16. The system of claim 15 wherein the processor is configured to indicate the secondary is empty when the comparison results in a difference reaching a first threshold and to indicate the primary is empty when the comparison results in a difference reaching a second threshold.

* * * * *